United States Patent [19]

Rhoads

[11] Patent Number: 4,838,688
[45] Date of Patent: Jun. 13, 1989

[54] HIGH SENSITIVITY CHROMATOGRAPHY DETECTOR

[76] Inventor: Robert Rhoads, c/o Spectrovision, Inc. 14 Alpha Rd., Chelmsford, Mass. 01824

[21] Appl. No.: 259,488

[22] Filed: Oct. 18, 1988

Related U.S. Application Data

[63] Continuation of Ser. No. 109,456, Oct. 16, 1987, abandoned.

[51] Int. Cl.$^4$ ............... G01N 21/05; G01N 21/64
[52] U.S. Cl. ................................ 356/72; 250/236; 250/458.1; 356/73; 356/236; 356/246; 356/318
[58] Field of Search ............... 356/72, 73, 236, 246, 356/317, 318, 440; 250/228, 458.1, 459.1, 461.1, 432 R, 576

[56] References Cited

U.S. PATENT DOCUMENTS

| | | | |
|---|---|---|---|
| 3,920,334 | 11/1975 | Steichen et al. | 356/73 |
| 4,422,761 | 12/1983 | Frommer | 356/246 X |
| 4,698,308 | 10/1987 | Ikeda | 250/458.1 X |

FOREIGN PATENT DOCUMENTS 61-132842  6/1986  Japan ................. 356/246

*Primary Examiner*—Vincent P. McGraw
*Attorney, Agent, or Firm*—M. Lawrence Oliverio

[57] ABSTRACT

A high sensitivity fluorescence and absorption detector comprising an elongated substantially cylindrical flow cell connected to and receiving the outflow of a fluid chromatography column; a mechanism for projecting a fluorescence generating beam of electromagnetic energy along on an axis substantially coincident with the axis of the flow cell; the flow cell including an elongated substantially cylindrical midsection housed by a tubular capillary transparent to the fluorescent radiation generated by the beam; a fluorescence integrating sphere completely surrounding the midsection of the capillary, the integrating sphere collecting at least about 3 pi steradian of the fluorescent radiation emanating through the capillary tube and into the sphere; the beam being projected to enter one end of the cylindrical flow cell, focus at about the center point of the axis of the cylindrical midsection, emanate through the other end of the flow cell and impinge upon a photodetector for detecting the portion of the beam which is not absorbed by the outflow flowing through the cell; the cross-sectional diameter and the axial length of the flow cell being selected such that the axially coincident beam which is projected into the cell and is not absorbed travels in its essential entirety along a direct or internally reflected path out of the other end of the cell; the integrating sphere having an aperture for allowing the fluorescent radiation which enters the sphere to emanate therethrough and impinge upon a fluorescence detector along a path offset from the axis of the cell.

10 Claims, 1 Drawing Sheet

HIGH SENSITIVITY CHROMATOGRAPHY DETECTOR

This application is a continuation of application Ser. No. 109,456, filed Oct. 16, 1987, now abandoned.

BACKGROUND OF THE INVENTION

The present invention relates to dual function absorption and fluorescence detectors for use in chomatography apparati and more particularly to a dual function detector having a highly sensitive fluorescence detection capacity.

Dual function absorption and fluorescence detectors for chromatography apparati such as described in U.S. Pat. No. 4,555,936 to Scott have been attempted whereby fluorescence detection in a sample flow cell of direct radiation is recorded. Despite technical promise, the successful implementation of high sensitivity fluorescence detection in a multifunctional detector apparatus has been severely restrained by the limitations imposed on the system which attempts to achieve a multitude of simultaneous detection functions in addition to fluorescence detection; and prior fluorescence analytical and detection systems such as discussed in U.S. Pat. Nos. 4,088,407 to Schoeffel; 3,920,336 to Sackett; 4,012,144 to Hedelman; 4,076,421 to Kishner; 3,869,208 to Lorenz; 3,874,799 to Isaacs; 4,278,887 to Lipshutz; 4,395,126 to Kramer; 3,937,962 to Faulhaber; 4,468,124 to Berick; 4,171,909 to Kramer; 4,006,990 to Munk; 4,220,415 to Staab; 4,540,281 to Akiyama; and 3,810,696 to Hutchins although theoretically useful in certain limited applications are not practically adaptable to or capable of achieving usefully sensitive fluorescence detection in a multifunctional chromatography detection assembly. As demonstrated by the prior art, highly efficient fluorescence collection has not been achievable generally and highly efficient fluorescence collection and detection in a multifunctional detector has not heretofore been attempted.

It is an object of the invention therefore to provide a novel geometric arrangement of chromatography absorption detector mechanisms together with a novel geometric fluorescence collector design which is simultaneously capable of achieving high sensitivity fluorescence and absorption detection.

SUMMARY OF THE INVENTION

In accordance with the invention there is provided a high sensitivity fluorescence and absorption detector comprising an elongated substantially cylindrical flow cell connected to and receiving the outflow of a fluid chromatography column; a mechanism for projecting a fluorescence generating beam of electromagnetic energy along on an axis substantially coincident with the axis of the flow cell; the flow cell including an elongated substantially cylindrical midsection housed by a tubular capillary transparent to the fluorescent radiation generated by the beam; a fluorescence integrating sphere completely surrounding the midsection of the capillary, the integrating sphere collecting at least about 3 pi steradian of the fluorescent radiation emanating through the capillary tube and into the sphere; the beam being projected to enter one end of the cylindrical flow cell, focus at about the center point of the axis of the cylindrical midsection, emanate through the other end of the flow cell and impinge upon a photodetector for detecting the portion of the beam which is not absorbed by the outflow flowing through the cell; the cross-sectional diameter and the axial length of the flow cell being selected such that the axially coincident beam which is projected into the cell and is not absorbed travels in its essential entirety along a direct or internally reflected path out of the other end of the cell; the integrating sphere having an aperture for allowing the fluorescent radiation which enters the sphere to emanate therethrough and impinge upon a fluorescence detector along a path offset from the axis of the cell.

Preferably the cylindrical midsection of the cell is mounted such that the midpoint of the axis of the cell coincides approximately with the center of the integrating sphere.

Most preferably the diameter of the flow cell is less than about 2 millimeters and the axial length of the flow cell is greater than about 5 millimeters.

The aperture in the integrating sphere is typically aligned along an axis which is approximately normal to the axis of the cell and which approximately intersects the midpoint of the axis of the midsection of the capillary. The integrating sphere is preferably conically sectioned along the axis of the flow cell on both ends of the capillary, the conical sections accounting for less than about one pi of the collection efficiency of the sphere.

In a most preferred embodiment the diameter of the aperture in the sphere is selected to allow between about 0.5 and about 0.8 pi steradian of fluorescent radiation entering the sphere to emanate directly through the aperture, between about 0.5 and about 0.8 pi steradian of fluorescent radiation entering the sphere to reflect once and emanate through the aperture and between about 1.4 and about 2.0 pi steradian of fluorescent radiation entering the sphere to be integrated by the sphere. The ratio of the surface area of the sphere to the surface area of the aperture is preferably less than about 9:1.

The invention minimizes radiation collection deficiencies normally inherent in integrating sphere technology in part by novel alignment of the fluorescence generating source with respect to the aperture and the spere generally. The aperture is selected to have a size relative to the sphere, and a positioning and distance relative to the fluorescence generating source which maximize collection and direction of the fluorescence emanating from the source to the photosensitive surface of a fluorescence detector.

DETAILED DESCRIPTION OF PREFERRED EMBODIMENTS

Figure 1:
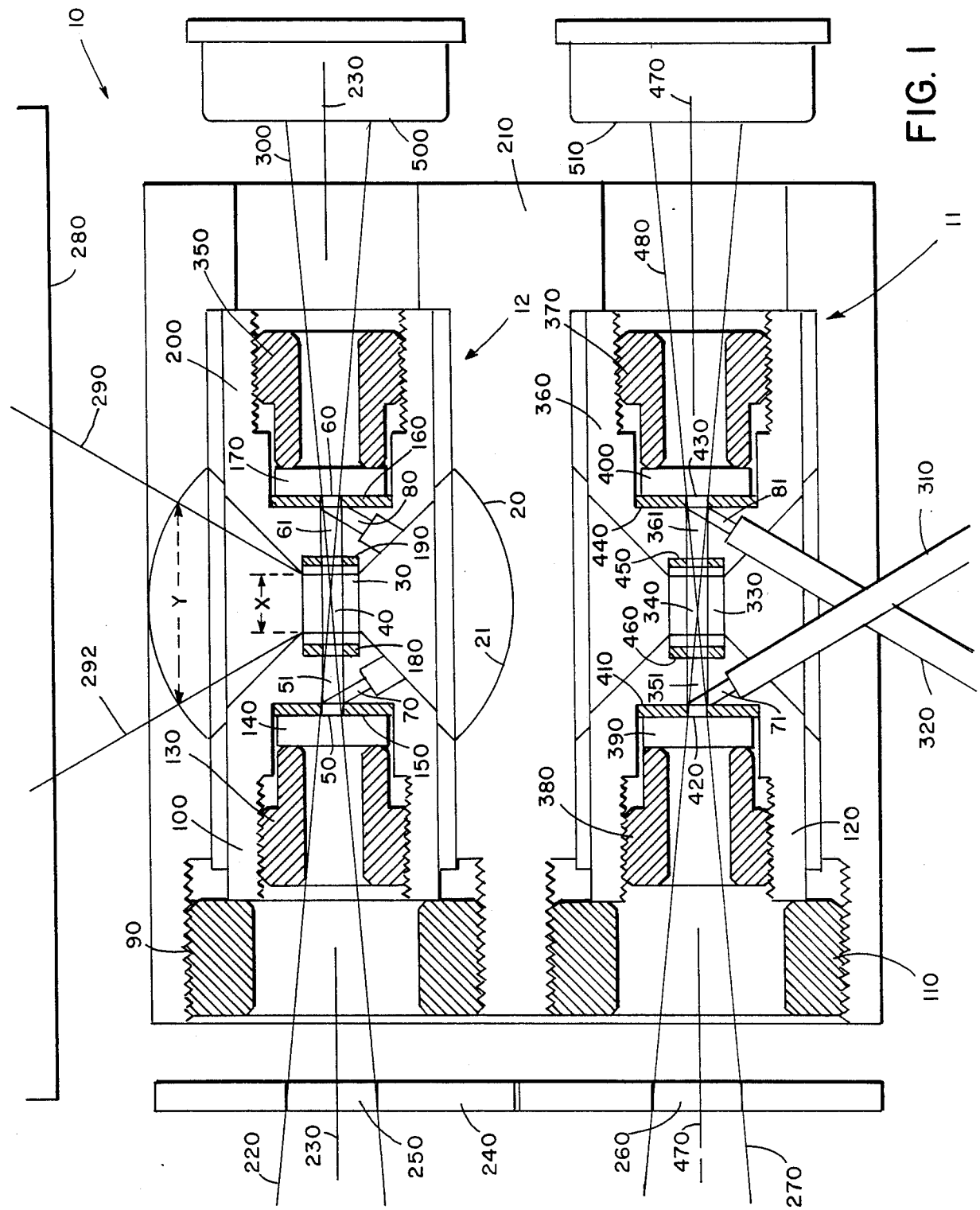
FIG. 1 is a cross sectional view of a detector assembly according to the invention showing a reference detector cell and a sample detector cell.

Following is a description of preferred embodiments of the invention.

FIG. 1 illustrates in cross-section a chromatography detector assembly 10 comprising a sample detector 12 and a reference detector 11. The two detectors 11, 12 are essentially identical in geometry, structure and operation except that the sample detector 12 includes an integrating sphere and a fluorescence sensitive detector 280.

A conventional source of polychromatic light (not shown) such as a xenon flash light source is typically employed to generate a beam of 210–650 mm wavelength light (not shown) which is directed through a conventional wavelength discriminator (not shown) such as a filter or a grating monochromator to generate a beam of light of pre-selected relatively discrete wavelength (energy) which is capable of generating fluorescence emission in certain classes of chemical species to be detected, if present, in a sample which is injected into a chromatography apparatus the outflow of which is directed through a sample flow cell provided in detector 10. The wavelength discriminator is selected to generate a beam of light having a relatively discrete wavelength which preferably falls somewhere in the range of about 220 to about 650 manometers. The beam of selected, relatively discrete wavelength light so generated is split by conventional means into two identical beams 220, 270, FIG. 1, of light which are separately focussed by conventional means at slits 250, 260 respectively provided in a light barrier 24 for purposes of further refining beams 220, 270 for more precise focussing through flow cells 51, 40, 61 and 351, 340, 361 of detectors 12 and 11 simultaneously.

Both of detectors 12, 11 comprise main absorption flow cell paths 51, 40, 61 and 351, 340, 361 respectively. Flow cell path 51, 40, 61 extends between the outside polished surfaces 50, 60 of a pair of discs 140, 170 which are transparent to the selected wavelength of beam 220. Similarly flow cell path 351, 340, 361 extends between the surfaces 420, 430 of discs 390, 400. Portions 51 and 61 of the sample detector 12 flow cell path are typically formed as cylindrical bores which are machine drilled in the ends of housings 100 and 200 respectively. Similarly portions 351 and 361 of the reference detector 11 are formed as cylindrical bores machine drilled in the ends of housings 120 and 360 respectively. A tubular capillary 30 having a central bore 40 is mounted in the ends of housings 100, 200 which have complementary receiving apertures machine drilled therein for receiving the respective ends of tubular capillary tube 30. The receiving apertures provided in the ends of housings 100, 200 are machine drilled such that when the respective ends of capillary 30 are mounted therein, central bore 40 is axially aligned with and mates with bores 51, 61 so as to form a continuous elongated flow cell absorption path extending from the front surface 51 of disc 50 to the front surface 61 of disc 60. Central bore 40 has the same inside diameter as bores 51 and 61. Capillary tube 30 comprises a material which is transparent to fluorescent radiation generated within bore 40 and preferably comprises a fused silica, quartz or other appropriate material which is transparent to fluorescent radiation, i.e. electromagnetic radiation having a wavelength between about 250 nm and about 650 nm.

Similarly, with respect to the reference detector assembly 11, flow cell path 351, 340, 361 comprises portions 351 and 361 which are preferably cylindrical bores machined into housings 120 and 360 respectively; and a capillary tube 350 having a central bore 340 with the same inside diameter is mounted in complementary receiving apertures provided in the ends of housings 120, 360 such that bores 351, 340, 361 are axially aligned and form a continuous, elongated reference flow cell absorption path, FIG. 1.

The transparent discs 140, 170, 390, 400, the front surfaces 50, 60, 420, 430 of which define the ends of absorption flow paths 51, 40, 61 and 351, 340, 361 respectively, are mounted in complementary apertures provided in housings 100, 200, 120 and 360 and are pressure held up against conventional fluid seals 150, 160, 410, 440, such as Kel-F, polytetrafluorethylene, or the like by threaded locking nuts 130, 350, 380, 370 which are in turn screwed into complementary threaded apertures provided in housings 100, 200, 120, 360 respectively. Fluid seals 150, 160, 410, 440 are provided with central apertures as shown in FIG. 1 for allowing the beams 220, 270 to project into the flow cell paths 51, 40, 61 and 351, 340, 361. As shown, the fluid seals 150, 160, 410, 440 provide a leakproof seal between the front surfaces 50, 60, 420, 430 and the housings 100, 200, 120 and 360. The housings 100, 200, 120, 360 are themselves aligned with respect to each other by appropriate mounting as shown within a master housing 210; and the housings 100, 200 and 120, 360 are pressure held toward each other, as shown, by threaded compression fittings 90, 110 which are screwed into complementary threaded apertures provided in master housing 210. Also as shown in FIG. 1 fluid seals 180, 190 and 460, 450 are typically provided between the ends of capillary tubes 30 and 330 and the rear faces of the receiving apertures provided in the ends of housings 100, 200 and 120, 360 for purposes of sealing the ends of the capillaries 30, 330 against fluid leakage. As shown in FIG. 1, seals 180, 190 and 410, 440 are also provided with central apertures for allowing beams 220 and 270 to project therethrough. Also as shown, fittings 90, 110, 130, 380, 350, 370 are all provided with appropriate apertures for allowing illumination beams 220, 270 and emanating beams 300, 480 to project entirely through the length of master housing 210.

Flow cell paths 51, 40, 61 and 351, 340, 361 are connected to fluid inlet tubes 70, 71 respectively and fluid outlet tubes 80, 81 respectively. Preferably tubes 70, 71 and 80, 81 are machine drilled into housings 100, 120, 200 and 360 respectively in the form of cylindrical apertures for receiving tubes which are independent of the housings such as tubes 310 and 320 as shown in FIG. 1. A tube, similar to tube 310, is sealably connected at one end to the outflow end of a chromatography column and is inserted at the other end into bore 70 thus directing the fluid outflow of a chromatoraphy column through sample flow cell path 51, 40, 61. An outlet tube similar to tube 320 is similarly inserted into machine drilled aperture 80 to receive the outflow of the fluid exiting through cell 51, 40, 61. As specifically shown in FIG. 1 a reference fluid flow tube 310, carrying the same fluid carrier which is used as the eluent through the chromatography column, is inserted into machine drilled aperture 71 and a reference outlet tube 320 is inserted into aperture 81. All such inlet and outlet tubes are typically silver soldered around the edges of apertures 71, 71, 80, 81 such that the tubes are sealably attached to the housings 100, 120, 200, 360 and whereby fluid does not leak out of the system As shown in FIG. 1, the beams 220, 270 of monochromatic light are focussed and narrowed by the slits 250, 260 and appropriate lenses to focus the beams 220, 270 at about the respective center points of the axes of capillary tubes 30 and 330. The overall length and diameter of the flow cell paths 51, 40, 61 and 351, 340, 361 is preferably selected to require that the widest angles of the photons of beams 220, 270 which may enter the flow cell paths 51, 40, 61 and 351, 340, 361 to be so close to parallel with the axes 230, 470 of the flow cell paths that the vast majority of any photon scattering which may occur within the cells will result in such scattered photons being internally reflected off of the inside surface of the capillary bores 40, 340, or the inside surface of the cells 51, 40, 61 and 351, 340, 361 generally. Such internal reflections thus minimize or eliminate the loss in sensitivity of the detectors 12, 11 due to photon scattering. The length of the flow cell paths 51, 40, 61 and 351, 340, 361 which is preferably selected to minimize such scattering losses is greater than about 5 millimeters (mm) and most preferably about 10 mm; and the diameter of the flow cell paths is preferably selected to be less than about 2 mm and most preferably about 1.5 mm.

As shown in FIG. 1 the axes 230, 270 of beams 220, 270 are preferably focussed and aligned to be coincident with the axes of flow cell paths 51, 40, 61 and 351, 340, 361 respectively. As the beams 220, 270 project through flow paths 51, 40, 61 and 351, 340, 361, the beams are partially absorbed by the fluids flowing therethrough and the unabsorbed portions 300, 480 of original beams 220, 270 project through the rear of housing 210. A pair of detectors 500 and 510 are mounted coaxial with the axes 230, 470 of the beams 220, 270, 300, 480 such that emanating beams 300, 480 impinge on the photodetector surfaces 500, 510. Photodetector 510 acts to detect and establish a zero line or reference absorption value for the fluid carrier and photodetector 500 records the amount of absorption by the fluid plus any absorption by any additional chemical components having flowed (eluted) out of the chromatography column and through cell 51, 40, 61. As is well known in the absorption chromatography art, the difference in photon detection between photodetector 500 and 510 is recorded over time on a conventional electronic recording mechanism.

As shown in FIG. 1, with reference to detector assembly 12 there is an elongated cylindrical midsection portion of capillary 30 and bore 40 having an axial length X which is not encompassed within the capillary receiving apertures provided on the ends of housings 100, 200. This elongated cylindrical portion of length X is surrounded by an integrating sphere 20. The curved inside surface 21 of the sphere is typically machine formed into the body of housing 210 such that the axis 230 of the midsection is aligned substantially coincident with a diameter line of the sphere and further such that the center point of the axis of the midsection of length X coincides with the center of sphere 20.

A circular aperture having a selected diameter Y is provided in sphere 20 for allowing radiation which fluoresces through the midsection of capillary 30 and into the volume of sphere 20 to be directed through the aperture and into impingement with the photosensitive surface of a photodetector 280. The circular aperture is most preferably selected such that its axis is normal to and intersects the midpoint of the axis of the midsection of bore 40. As shown in cross section in FIG. 1, the dashed line Y represents a diameter of such an aperture in sphere 20. Lines 290, 292 represent a cross section of the conical volume through which fluorescence radiation must travel in order to pass through the aperture and impinge on photodetector 280.

Sphere 20 is designed to direct at least about 3 pi steradian of the fluorescent radiation which emanates through the midsection of capillary 30 and into the volume of sphere 20, through the aperture and into impingement with photodetector surface 280. As shown in FIG. 1, the sphere is machined into housing 210 such that there are two opposing blank conical sections whose axes are coincident with axis 230. By the same token, there remains an incomplete integrating sphere 20 extending 360 degrees around the midsection having an inner surface 21 which is coated with an appropriate reflective coating such as magnesium fluoride, polished aluminum, gold, silver or the like. As can be seen from FIG. 1, any fluorescence radiation which projects along an angle toward one of the two blank conical sections is not captured by the incomplete integrating sphere 20. The completeness of sphere 20, and a fortiori, the size of the blank conical sections, is selected such that the sphere 20 has a collection efficiency with respect to fluorescence entering the volume of sphere 20 of at least about 3 pi steradian.

Most preferably the surface 21 completeness of the sphere 20, i.e. the diameter Y of the aperture, the diameter of the sphere 20 and the size of the blank conical sections, are selected such that between about 0.5 and about 0.8 pi steradian of the fluorescence entering sphere 20 is emitted directly from the bore 40 and through the aperture, between about 0.5 and about 0.8 pi steradian of the fluorescence entering sphere 20 reflects once off of surface 21 and is then directed through the aperture in the sphere 20 and between about 1.4 and about 2.0 pi steradian of the fluorescence entering sphere 20 is integrated by the sphere 20, i.e. reflects off of surface 21 more than once and is ultimately directed through the aperture after such multiple reflections. It is noted that the theoretical limit of an integrating sphere's collection efficiency is 4 pi steradian. Most preferably the ratio of the surface area of the sphere to the area of the aperture is less than about 9:1 and the completeness of the surface area of the sphere is at least about 50%, i.e. a complete sphere minus the surface area eliminated by the aperture and the blank coaxial conical sections.

By virtue of the use of a relatively elongated cylindrical midsection X and the coaxial alignment of the blank conical sections, the size of the blank conical sections may be minimized and the direction of the total amount of fluorescence occurring in the midsection X into the volume of the sphere 20 may be maximized. Most preferably the blank conical sections coaxially aligned with the axis 230 are selected to be of such a size to eliminate less than about 25% of the otherwise complete sphere 20 i.e. as if the sphere included the surface area eliminated by the aperture. In a preferred embodiment of the invention the midsection length X is between about 2 and about 4 mm, the diameter of the aperture Y is less than about 0.3 inches and the diameter of the sphere is greater than 0.7 about 0.7 inches.

It will now be apparent to those skilled in the art that other embodiments, improvements, details, and uses can be made consistent with the letter and spirit of the foregoing disclosure and within the scope of this patent, which is limited only by the following claims, construed in accordance with the patent law, including the doctrine of equivalents.

What is claimed is:

1. A high sensitivity fluorescence and absorption detector comprising:
   a substantially cylindrical flow cell connected to and receiving the outflow of a fluid chromatography column, the flow cell comprising a cylindrical capillary transparent to fluorescent radiation;
   a housing comprising forward and rearward housing sections, each housing section including means for mounting one end of the capillary therein, the forward and rearward housing sections being spaced apart by the capillary mounted therebetween in the mounting means, the housing sections being configured around the capillary in the shape of a sectioned sphere;

means for projecting a fluorescence generating beam of radiation along an axis substantially coincident with the axis of the flow cell, the beam being projected to enter one end of the flow cell, focus at about the center point of the axis of the capillary, emanate through the other end of the flow cell and impinge upon a photodetector for detecting the portion of the beam which is not absorbed by the outflow flowing through the cell;

the surface of the housing sections around the capillary being reflective to fluorescent radiation and reflecting essentially all fluorescent radiation which emanates through the capillary and onto the surfaces of the housing sections through an aperture provided in the housing sections along a path offset from the axis of the flow cell;

the capillary being mounted in the housing sections such that the axial midpoint of the capillary coincides approximately with the center of the sectioned sphere formed by the housing sections;

the flow cell having a cross-sectional diameter and an axial length selected to cause the essential entirety of the beam directed into the flow cell and not absorbed to be directed along a direct or internally reflected path out of the flow cell;

the axis of the flow cell being disposed along and within the limits of a diameter of the sectioned sphere formed by the housing sections.

2. The detector of claim 1 wherein the area of the spherically configured surface of the housing section is selected to collect at least about 3 pi steradian of the fluorescent radiation emanating through the capillary.

3. The detector of claim 2 wherein the diameter of the flow cell is less than about 2 millimeters and the axial length of the flow cell is greater than about 5 millimeters.

4. The detector of claim 2 wherein the aperture in the housing sections is aligned along an axis which is approximately normal to the axis of the cell and which approximately intersects the midpoint of the axis of the midsection of the capillary.

5. The detector of claim 2 wherein the housing sections are conically sectioned along the axis of the flow cell on both ends of the capillary, the conical sections accounting for less than about one pi of collection efficiency.

6. The detector of claim 4 wherein the housing sections are conically sectioned along the axis of the flow cell on both ends of the capillary, the conical sections accounting for less than about one pi of collection efficiency.

7. The detector of claim 5 wherein the diameter of the aperture in the housing sections is selected to allow between about 0.5 and about 0.8 pi steradian of fluorescent radiation impinging on the spherically formed surfaces of the housing sections to emanate directly through the aperture, between about 0.5 and about 0.8 pi steradian of fluorescent radiation to reflect once and emanate through the aperture and between about 1.4 and about 2.0 pi steradian of fluorescent radiation to be integrated by the spherically formed surfaces of the housing sections.

8. The detector of claim 6 wherein the diameter of the aperture in the housing sections is selected to allow between about 0.5 and about 0.8 pi steradian of fluorescent radiation impinging on the spherically formed surfaces of the housing sections to emanate directly through the aperture, between about 0.5 and about 0.8 pi steradian of fluorescent radiation to reflect once and emanate through the aperture and between about 1.4 and about 2.0 pi steradian of fluorescent radiation to be integrated by the spherically formed surfaces of the housing sections.

9. The detector of claim 7 wherein the ratio of the surface area of the spherically formed surfaces of the housing sections to the area of the aperture is less tan about 9:1.

10. The detector of claim 8 wherein the ratio of the surface area of the spherically formed surfaces of the housing sections to the area of the aperture is less than about 9:1.

* * * * *